United States Patent [19]
Jegers et. al.

[11] Patent Number: 4,729,375
[45] Date of Patent: Mar. 8, 1988

[54] MODULAR CONTROL FOR TANNING BEDS

[75] Inventors: Viktor J. Jegers, Bloomington; Joseph E. Suppler, Golden Valley, both of Minn.

[73] Assignee: Sun Time, Inc., Plymouth, Minn.

[21] Appl. No.: 729,958

[22] Filed: May 2, 1985

[51] Int. Cl.$^4$ .............................................. A61N 5/06
[52] U.S. Cl. .................................... 128/376; 128/395; 315/360; 361/334; 361/394
[58] Field of Search ........................ 128/376, 395, 396; 315/360; 361/331, 332, 334, 392, 393, 394, 333

[56] References Cited
U.S. PATENT DOCUMENTS

| 2,567,740 | 9/1951 | Smith | 361/334 X |
| 2,788,470 | 4/1957 | Giel et al. | 361/394 |
| 3,483,543 | 12/1969 | Flanagan | 361/394 |
| 4,283,661 | 8/1981 | Doty | 315/360 |

Primary Examiner—Anton O. Oechsle
Attorney, Agent, or Firm—Palmatier & Sjoquist

[57] ABSTRACT

A modular timer assembly for controlling tanning beds and alike including a power supply module and a plurality of removably attached timer modules affixed between end panels; the timer modules using reduced voltage current to control the external tanning beds; and an extendable means supplying line voltage and reduced voltage current to each module.

12 Claims, 8 Drawing Figures

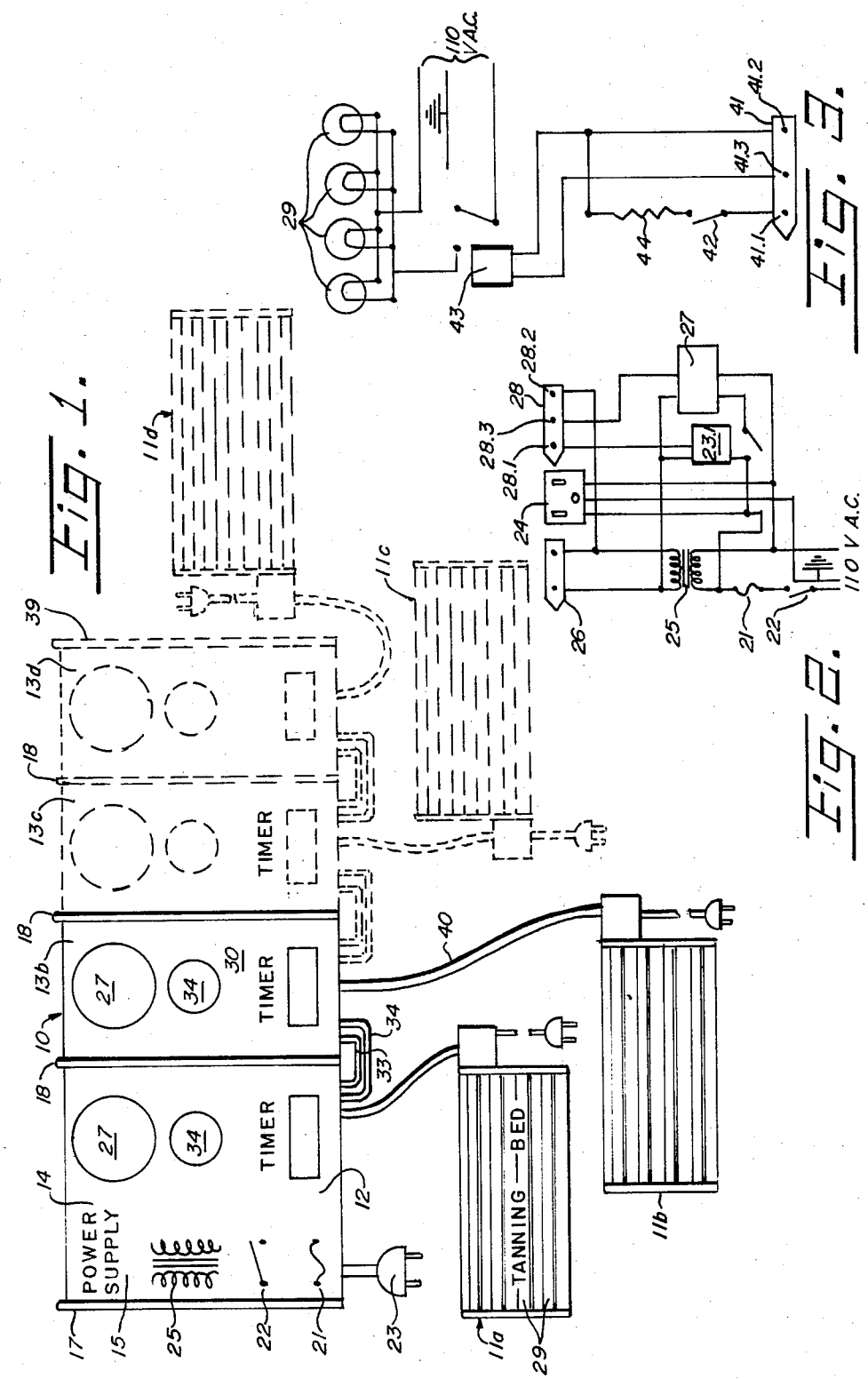

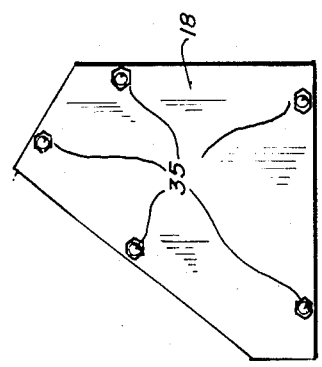
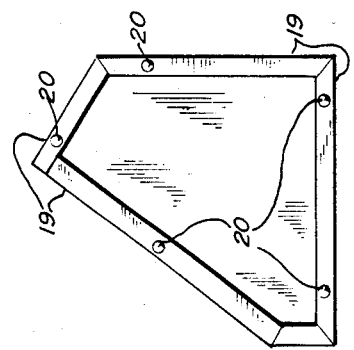
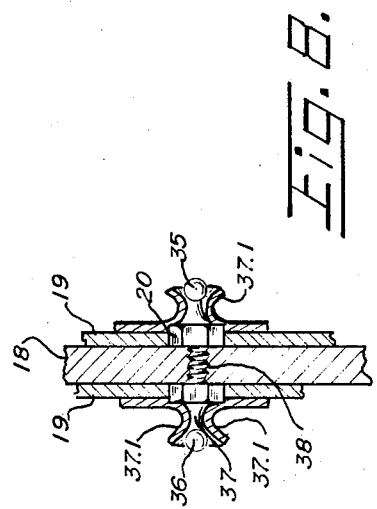
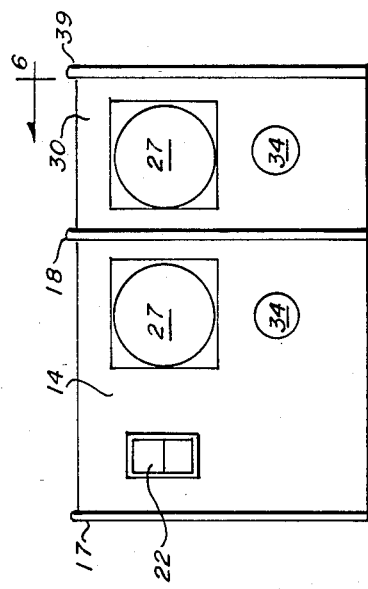
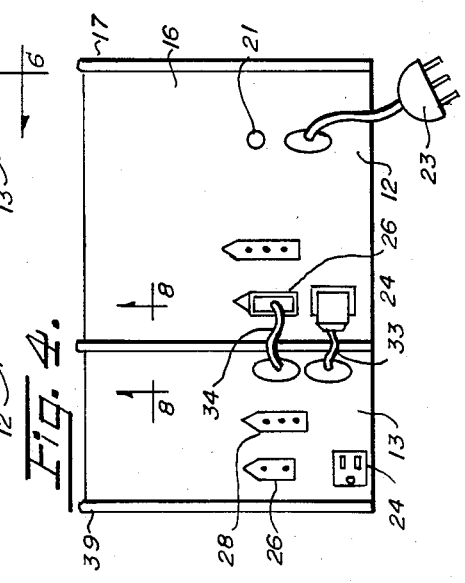

MODULAR CONTROL FOR TANNING BEDS

BACKGROUND OF THE INVENTION

The invention relates to modular timer for remotely controlling multiple tanning beds. Timing devices, typically, have been designed to control a fixed number of electrical devices. Typically, the timer controls either one or a fixed number of tanning beds.

The currently popular tanning salons have a reception area where the customers enter and multiple private booths with tanning beds. The tanning booths are usually some distance from the reception area for convenience of the salon operator and to provide privacy in the individual tanning booths.

It is advantageous for the salon operator to control the time the tanning lights can be energized on each tanning bed assuring the customer receives the maximum tanning action while avoiding unnecessary risk of burning from overexposure to the tanning lamps. Additionally, by controlling the time the customer spends in the tanning booth, the salon can increase its profits.

When using the single booth timers, the operator purchases a complete timer unit for each of the tanning booths currently operating. This practice wastefully duplicates some functions in each of the timers. Also, the multiple single unit timers tend to be larger and waste counter space even when efficiently arranged. Each timer must each be connected to a source of electrical power which often leads to numerous tangled electrical cords leading to a limited number of electrical outlets.

Multiple booth timer control units contained in a single cabinet are available. The multiple control units require the salon operator to purchase the large timer assembly to control only one tanning booth. This practice is both wasteful of counter space and uneconomical.

The multiple booth control units additionally usually cannot have timers added in the field requiring the timer and therefore the tanning booth it controls be taken out of service when additional timers are added. More importantly, when one timer requires repairs the entire timer assembly becomes unusable while the one timer is repaired.

Some single unit and multiple unit timers use line voltage (110 Volts a.c.) to control the remote tanning beds. When line voltage is used as such, the wiring must be done according to the prevailing Electrical Code and often requires inspection before the additional units can be put into service adding costs each time tanning booths are added to the salon.

SUMMARY OF THE INVENTION

An object of the invention is to provide an attractive, modular expandable tanning booth timer where additional timer modules can be easily and readily added when additional tanning beds are added to the salon.

Another object of the invention is to provide a modular controller using low voltages to control the remote tanning beds.

A feature of the invention is a modular timer assembly where a single power supply is adapted to provide the electrical current to a variable number of timer modules controlling the tanning beds. The power supply and timer modules are constructed in modular cases facilitating addition or replacement of the modules.

The power supply module contains a step down transformer supplying a reduced voltage current to the timers. A power switch and a fuse are affixed to the power supply case. The timer and timer reset controls are affixed to the front face of the power supply case integrating the first timer into the power supply module.

End panels are affixed to the open ends of the power supply case. The end panel adjacent the power supply is permanently attached to the power supply case and has its base flush with the base of the power supply case and extends outward past the remaining four edges of the power supply case.

At the timer end of power supply case a similarly shaped end panel is removably attached. The removable end panel is attached using five ball studs extending into five spring loaded sockets within the module case.

The rear panel of the power supply case has a power supply connector for connection into a 110 volt a.c. line current. Sockets are provided for supplying both 110 volt and reduced voltage to the timer modules.

Each timer module contains a resettable timer for a tanning booth and the associated timer reset button and total hour meter. On the rear panel of each timer module are connection plugs supplying line voltage and reduced voltage to the timer module and line voltage and reduced voltage sockets for supplying current to an adjacent timer module. A three prong socket for receiving the tanning bed controller cord is also provided.

A tanning bed controller is attached to each tanning bed. The tanning bed controller has a normally open start switch actuated by movement of the tanning lamp assembly controlling current supplied to the timer motor. When energized, the timer also actuates a relay in the tanning bed controller supplying current to the tanning bed lamps.

The divider panels are a continuous panel covering the end of each module and separating the adjacent modules preventing an operator from exposing himself to the multiple current carrying terminals in several modules.

A divider panel is placed between two modules. The divider panel has dimensions to fit between and adjacent the modules having its base flush with the module base and extend outwardly past the remaining edges of the modules separating the modules.

The divider panel has five male ball studs attached on each of its surfaces extending into and releasably retained by the five female spring loaded sockets on the ends of the modules. The ball studs and sockets cooperate to attach each module to a divider panel and each divider panel to its two adjacent modules thereby connecting the modules together.

In use the power supply module is installed by placing it and a suitable number of timer modules on a convenient counter top. The timer modules line voltage and reduced voltage cords are then connected to the sockets in the adjacent sockets. The tanning booths using the low voltage lines control cords.

The removable end panel can be readily removed by moving it away from its end releasing the ball studs from their sockets. Likewise, a divider panel can be readily installed by placing it adjacent the timer case and urging its ball studs into the sockets in the power supply case.

When additional tanning booths are to be controlled, additional timer modules are added by first removing the timer module end panel and attaching a divider panel. The additional timer module is attached to the divider panel extending the timer assembly.

The additional timer module is placed adjacent the divider panel and the ball studs of the dividing panel urged into the mating sockets of the timer case. When the necessary number of timer modules have been so installed the original timer end panel is replaced on the far end of the modules.

Each timer panel so installed is electrically connected simply by inserting the low voltage and 110 volt power cords into the polarized sockets of the adjacent module. The added timer modules can then be connected to their respective tanning booths with the tanning bed control cord.

Thus the installation of a number of timers to control a number of tanning booths can be readily be done in the tanning salon and requiring minimal skill.

In use low voltage current switched by the start switch energizes the timer and the relay controlling the tanning lamps. The lamps turn on when the customer reclined in the tanning bed moves the lamp assembly into its operating position closing the start switch and starting the timer to actuate the tanning lamps. After the preset time expires, the timer turns off the tanning lamps.

The principal advantage of the invention is it provides a modular expandable tanning booth timer where additional timer modules can be easily and readily added when additional tanning booths are added to the salon.

Another advantage of the invention is that it provides a modular controller using low voltages to remotely control a tanning booth.

BRIEF DESCRIPTION OF THE DRAWINGS

FIG. 1 is an overall diagrammatic view showing the modular timer assembly and tanning beds, and showing in dotted lines, additional timer modules for tanning beds.

FIG. 2 is an electrical schematic diagram of the circuit of the master controller.

FIG. 3 is an electrical schematic diagram of circuit of on tanning bed.

FIG. 4 is a front elevational view of the modular timer assembly with on timer module attached.

FIG. 5 is a rear elevation of the timer assembly with one timer module attached.

FIG. 6 is an end view of one module taken approximately at 6—6 of FIG. 4.

FIG. 7 is an elevational view of one divider panel.

FIG. 8 is an enlarged detailed cross sectional view of the ball stud connectors taking approximately at 8—8 of FIG. 5.

DETAILED SPECIFICATION

FIG. 1 diagrammatically shows the timer assembly 10 and a plurality of connected tanning beds 11a–11d. Timer assembly 10 has a power supply module 12 and one or more timer modules 13b–13d. The power supply module 12 has an elongate metallic case 14 having a rearwardly sloping front face 15 and a vertical rear face 16. The terminal end panel 17 is attached to one side of the power supply module 12. A divider panel 18 is removably attached to the second end of the power supply module 12. The power supply module case 14 has perpendicular connector tabs 19 on its each end with stud sockets 20 affixed on the interior of the connector tabs.

The power supply module 12 also contains the electrical power supply for supplying line voltage current and reduced voltage current to each timer assembly as shown schematically in FIG. 2. Electrical power supply has a power switch 22 for interrupting the current supply and a fuse 21 preventing excess current flow from its power plug 23.

Each timer module 13 is contained in a timer case 30 having a rectangular base and a rearwardly sloping front face 31. Each timer case 30 has end dimensions identical to the power supply module 12. Attached to the front face 31 is the timer 27 and its reset switch 34. Each timer case 30 has perpendicular end connector tabs 19 on its each end with stud sockets 20 affixed on the interior of the connector tabs 19. The line voltage is supplied through a relay operated timer switch 23.1 to the time 27 contained in the module 12, 13 and to rear mounted plug 24 for supply to the additional timer modules 13. The line voltage is also transformed to a reduced voltage, preferably 24 volts, using the transformer 25. Reduced voltage from the transformer 25 is supplied to a polarized outlet plug 26 for supply to additional timer modules 13.

Reduced voltage from the transformer 25 or the reduced voltage supply cord 34 is supplied to the timer 27 and through the timer relay 23.1 to the first conductor 28.1 of the three pronged polarized tanning bed connector 28 for controlling the lamps 29 of the tanning bed 11a.

The bed controller, shown schematically in FIG. 3, is connected through the bed control cord 40 and its plug 41 to the bed connector socket 28. The bed controller has a start switch 42 and a resistor 44 serially connected between the first conductor 41.1 and the second conductor 41.2 of the tanning bed cord 40. The start switch 42 is a normally open switch operable in response to moving the tanning lamps into their operational position.

When closed, the start switch 42 allows the reduced voltage current to flow therethrough energizing the timer relay and closing the timer switch 23.1 to allow line voltage current to flow to operate the timer 27. With the timer 27 operating, current is supplied to the third conductor 28.3 of the bed connector plug 28 and thence to the third conductor 41.3 of the tanning bed cord 40 to the lamp relay 43. When energized, the lamp relay 43 closed its normally open switch supplying line voltage current to the tanning lamps 29.

It is understood that when the tanning lamps 29 are moved from their operational position, the start switch 42 is opened stopping the timer 27 and turning off the tanning lamps 29. Also, when the preset time set on the timer 27 elapses, no current is supplied to the third conductor 28.3, 41.3 and to the lamp relay 43 thereby turning off the tanning lamps.

A divider panel 18 fits between the power supply module 12 and the first timer module 13b and between each successive timer modules 13. The divider panel 18 has dimensions to abut the end connector tabs 19 of the power supply module 12 or timer module 13 so as a respective bases are flush and the divider panel 18 extends outwardly at the other sides of the module.

The divider panel 18 may be open in its central portion and constructed of a suitable rigid material. The divider panel 18 is preferably constructed from a continuous sheet of one-eighth inch aluminum restricting operator access to the interior of the timer modules 13.

A plurality, preferably 5, ball studs 35 extend outwardly from each side of the divider panel 18. The ball studs 35 are located on a divider panel 18 so as to mate with the stud sookets 20 on the end connector tabs 19 of the module. Ball studs 35 may be attached by any suitable means and are preferably attached using a threaded bolt 38 passing through the divider panel 18 and retaining each ball stud 35.

The ball studs 35 have a round head 36 and a reduced diameter neck 37. The ball stud head 36 passes into the stud socket 20 and is retained therein by the tension of the socket springs 37.1 on the interior of the connector tabs 19.

A removable end panel 39 is attached to the end of the timer assembly opposite the terminating end panel 17. The end panel 39 has identical dimensions to the divider panel 18 and is likewise preferably constructed from continuous sheet of one-eighth inch aluminum. The end panel 39 has a plurality, preferably 5, ball studs 35 extending from its one side located to mate with the stud socket 20 in the last timer module case 30.

In its use the power supply module 12 and the appropriate number of timer modules 13 are assembled. The modules are assembled by removing the end panel 39 from, the power supply module 12. A first divider panel 18 is then placed adjacent the power supply module 12 and its ball studs 35 are urged into the mating sockets 20 on the end tab 19 of the power supply module 12.

In assembly, the ball studs 35 are urged into the stud sockets 20. The ball stud head 36 moving the socket springs 37.1 aside allowing the ball stud head 36 to pass between the socket springs 37.1 and disposing the reduced diameter neck 37 between the socket springs 37.1 where the ball stud 35 is retained by the tension of the socket spring 37.1 against the ball stud head 36.

The first timer module 13b is placed adjacent the first divider panel 18 and the ball studs 35 of the divider panel 18 are urged into the sockets 20 in the end tabs 19 of a timer module case 30 where the ball stud heads 36 are retained against the tension of the socket springs 37.1.

Additional timer modules 13c, 13d may be added when needed. With the proper number of timer modules 13 attached adjacent the power supply module 12 the end panel 39 is attached to the end of the last timer module 13 by placing it adjacent and urging the ball studs 35 into the stud sockets 20 in the connector tabs 19 in the timer case 30.

The first timer module 13b is electrically connected from power supply module 12 by connecting its line voltage cord 33 into the line voltage socket 24 of the power supply module 12. The reduced voltage cord 34 of the timer module 13b is then plugged into the reduced voltage socket 26 of the power supply module 12.

Each successive timer module 13 is similarly connected placing the plug of the line voltage cord 33 into the adjacent line voltage socket 24 and the plug of the reduced voltage cord 34 into the adjacent reduced voltage socket 26. Timer assembly is thus assembled and is prepared for connection through the tanning bed connector 41 to the tanning bed 11.

The tanning beds 11 are connected through the tanning bed control cord 40 which terminates three connector polarized plug 41 adapted to fit into the bed connector 28 on the rear face 16 of the power supply module 12 or the rear face of a timer module 13.

The timer assembly 10 may now be connected using the power supply cord 23 to a source of line current and turned on using the power switch 22 ready for use.

In use the timer 27 is set for the appropriate tanning time for the client. The client retires to a distant tanning booth where he prepares for the tanning session. After the client is reclined in the tanning bed 11 the lamp assembly is moved into its operational position thereby closing the start switch 42, schematically shown in FIG. 3, energizing the timer relay 23.1 and starting the timer 27. As the timer 27 operates it energizes the lamp relay 43 starting the tanning lamps 29.

After the time pre-set on the timer 27, timer circuit opens de-energizing the lamp relay 43 and the tanning lamps 29 turn off. Additionally, during the tanning session should the client move the tanning lamps 29 from their operative position the start switch 42 is opened de-enerizing and stopping the timer 27. The client may then return the tanning lamps 29 to their operative position closing the start switch 42, restarting the timer 27, and continuing his tanning session.

When the salon operator installs additional tanning beds, additional timer modules 13 are added to control the additional beds by removing the terminal end panel 39 and installing additional divider panels 18 and timer modules 13 and replacing the terminal end panel.

The added timer modules 13 are electrically connected by inserting their line voltage cord 33 into the adjacent line voltage outlet 24 and the reduced voltage cord 34 into the adjacent reduced voltage outlet 26. The plug 41 on the cord 40 of the additional tanning beds 11 is inserted into the bed connector 28 completing the installation.

If one on the timer modules 13 requires repairs, the one timer module 13 can easily be removed and serviced without effecting the operation of the remaining timer modules 13. The inoperative timer module 13 is removed by disconnecting the line voltage cord 33 and the reduced voltage cords 34 from the inoperative timer. Once electrically disconnected, the timer module 13 can be removed from the timer assembly 10 by applying force to move the adjacent divider panels 18 from the ends of the timer module 13. The movement will withdraw the ball studs 35 from the stud sockets 20 releasing the ball studs 35 so the inoperative timer module 13 can be removed for service. After the inoperative timer 13 is removed, the timer assembly 10 is reassembled without the inoperative timer module 13 remaining serviceable with one fewer timer module 13.

The present invention may be embodied in other specific forms without departing from the spirit or central attributes thereof, it is therefore desired that the present embodiment be considered in all respects as illustrative and not restrictive, reference being made to the appended claims rather than the foregoing description to indicate the scope of the invention.

What is claimed is:

1. A modular timer assembly having a power supply module and at least one timer module for controlling a plurality of tanning beds comprising, an extendable electrical control means having a line current source and a plurality of electrical outlets, each outlet cooperatively controlling the lights of one tanning bed, each module having a modular case confining the electrical control means, each modular case having one electrical outlet for timing one tanning bed and having divider panels spanning the interspace between each modular case, each divider panel and modular case having confronting attachment faces, the attachment faces further having affixed cooperating male and female connectors so that the male connectors of the one face are retained by the adjacent female connectors removably retaining the divider panels in the interspaces between the modular cases.

2. The modular timer assembly according to claim 1 and the electrical control means further comprising a transformer providing reduced voltage output current to each outlet.

3. The modular timer assembly according to claim 2 and the reduced voltage output current is twenty-four volts.

4. The modular timer assembly according to claim 1 and the cooperating male and female connectors are ball stud connectors.

5. The modular timer assembly according to claim 4 and the male ball stud connectors are affixed to the panel attachment faces and the female ball stud connectors sockets are affixed to the attachment faces of the modular cases.

6. The modular timer assembly according to claim 5 and there are five ball stud connectors on each panel attachment face.

7. A modular timer assembly for a tanning bed having a power supply module and at least one timer module comprising,
    an elongate power supply module case, closed to one end, having a current supply means providing a switchable source of current at line voltage and a reduced voltage;
    each timer module having an elongate timer module case fitting adjacently spaced from the power supply case end and having a timer therein, the timer electrically communicating with the current supply means, and further having an external start switch, the start switch being operable to start and stop the timer, and having means connecting the tanning lights so as the tanning lights are energized concurrently with the time;
    at least one divider panel fitting between two modules abutting and covering the respective ends thereof;
    a cooperative connection means on the ends of the cases and the sides of the panels releasably retaining the respective case end confronting the respective panel side linearily aligning the adjacent modules and connected through the panel retained therebetween;
    a terminal end panel dimensioned to abut and cover the one end of the one timer module most remote from power supply module.

8. The modular timer assembly in claim 7 with a plurality of timer modules and having the power supply module and the first timer module both contained within an elongate power supply module case.

9. The modular timer assembly in claim 7 and the cooperative connection means is cooperating male and female ball stud connectors.

10. The modular timer assembly according to claim 7 and the male ball stud connectors are affixed to the panel sides and the female ball stud connectors sockets are affixed to the ends of the modular cases.

11. The modular timer assembly according to claim 9 and there are five ball stud connectors on each side of each divider panel.

12. A modular timer assembly for controlling tanning beds comprising:
    a power supply module having an elongate five-sided case with perpendicularly inwardly extending attachment tabs at one end, the attachment tabs having five ball stud sockets affixed thereon, and having an inclined front face with a power switch and a fuse affixed thereon, a base, and a rear face, an electrical power supply confined within the power supply case, the electrical power supply having a cord with attached plug for supplying line voltage current through the power switch and the fuse to a transformer and to a line voltage socket affixed to the rear panel of the module case, the transformer producing twenty-four volt electrical current supplied to a polarized reduced voltage socket affixed on the rear panel of the module case;
    at least one tanning bed module having a start switch in series with a resistor, a tanning lamp relay, and a three conductor bed connector cord with attached polarized plug, the start switch operable in response to movement of the tanning lamps so that movement of the tanning lamps into operational position closed the start switch allowing current to flow from the first conductor of the bed connector cord through the switch and resistor to the second conductor of the bed connector cord, the lamp relay controlling a normally open switch in a line voltage supply to the tanning bed lamps and further being connected between the second and third conductor of the bed connector cord;
    at least one timer module having an elongate five-sided case with perpendicularly inwardly extending attachment tabs at each end, the attachment tabs having fivr ball stub sockets affixed thereon, and hving an inclined front face with a timer and a timer reset affixed thereon, a base, and a rear face, a reduced voltage cord insertable into the reduced voltage socket supplying reduced voltage current to the timmer relay and to the reduced voltage socket affixed to the rear face of the timer case, a line voltage cord insertable into the line voltage socket supplying line voltage current through a timer relay to the timer and to a line voltage socket affixed to the rear face of the timer case, a three conductor bed connector socket affixed to the rear face of the timer case, the timer relay connected between the first and second conductors of the bed connector controlling a normally open switch operable in response to the start switch on the bed controller so that closing the start switch energized the timer relay closing the normally open switch to supply line voltage current to the timer, the timer having a setable means for measuring time while line voltage current is supplied thereto and means supplying reduced voltage to the third conductor of the bed connector while measuring said time;
    at least one planar five-sided divider panel having edges and faces, and having dimensions to abut and overlie the end of the module case being flush at the base and extending outwardly at the other four edges, each face having five male ball stub connectors extending outwardly from the face and affixed thereto, the ball stub connectors located to be removably insertable in the ball stub sockets of the module case attachment tabs;
    a planar five-sided end panel having edges and faces, and having dimensions to abut and overlie the end of the power supply module or timer module case being flush at the respective base and extending outwardly at the other four edges, the one face of said end panel having five male ball stud connectors extending outwardly from the face and affixed thereto, the ball stub connectors located to be removably insertable in the ball stud sockets of the module case attachment tabs so that the one end panel is selectively attachable to either said one end of the power supply module or the end of the timer module which is most remote from the power supply module.

* * * * *

UNITED STATES PATENT AND TRADEMARK OFFICE
CERTIFICATE OF CORRECTION

PATENT NO. : 4,729,375
DATED : March 8, 1988
INVENTOR(S) : Viktor J. Jegers, Joseph E. Supplee It is certified that error appears in the above-identified patent and that said Letters Patent is hereby corrected as shown below: On the Title Page, Item [75], "Suppler" should read --Supplee--.

Column 3, line 43, delete "on" and replace it with --one--.

Column 3, line 45, delete "on" and replace it with --one--.

Column 7, line 29, delete "to" and replace it with --at--.

Column 7, line 42, delete "time;" and replace it with --timer;--.

Column 8, line 24, delete "closed" and replace it with --closes--.

Column 8, line 31, delete "conductor" and replace it with --conductors--.

Column 8, line 35, delete "fivr" and replace it with --five--, and delete "stub" and replace it with --stud--.

UNITED STATES PATENT AND TRADEMARK OFFICE
CERTIFICATE OF CORRECTION

PATENT NO. : 4,729,375

DATED : March 8, 1988

INVENTOR(S) : Viktor J. Jegers, Joseph E. Supplee

It is certified that error appears in the above-identified patent and that said Letters Patent is hereby corrected as shown below:

Column 8, line 36, delete "hving" and replace it with --having--.

Column 8, line 62, delete "stub" and replace it with --stud--.

Column 8, line 64, delete "stub" and replace it with --stud--.

Column 8, line 65, delete "stub" and replace it with --stud--.

Column 9, line 6, delete "stub" and replace it with --stud--.

Column 10, line 5, add a space between "from" and "the".

Signed and Sealed this

Twenty-first Day of March, 1989

*Attest:*

DONALD J. QUIGG

*Attesting Officer*  Commissioner of Patents and Trademarks